US011320369B2

(12) United States Patent
Kormann et al.

(10) Patent No.: US 11,320,369 B2
(45) Date of Patent: May 3, 2022

(54) AGRICULTURAL SAMPLING APPARATUS AND SYSTEM

(71) Applicant: Deere & Company, Moline, IL (US)

(72) Inventors: Georg Kormann, Zweibrücken (DE); Wolfram Haiges, Magstadt (DE); Peter Schade, Bad Dürkheim (DE); Nico Correns, Mannheim (DE); Bernhard Fischer, Tiefenbronn (DE); Fred Grunert, Mannheim (DE)

(73) Assignee: DEERE & COMPANY, Moline, IL (US)

( * ) Notice: Subject to any disclaimer, the term of this patent is extended or adjusted under 35 U.S.C. 154(b) by 522 days.

(21) Appl. No.: 16/053,514

(22) Filed: Aug. 2, 2018

(65) Prior Publication Data

US 2019/0170640 A1  Jun. 6, 2019

(30) Foreign Application Priority Data

Aug. 2, 2017  (DE) .......................... 102017213419.4

(51) Int. Cl.
*G01J 3/28* (2006.01)
*G01N 21/31* (2006.01)
(Continued)

(52) U.S. Cl.
CPC ......... *G01N 21/3151* (2013.01); *A01B 76/00* (2013.01); *A01C 7/10* (2013.01);
(Continued)

(58) Field of Classification Search
CPC .. G01N 21/3151; G01N 21/255; G01N 21/65; G01N 33/0098; G01N 2033/245; G01N 2201/063; G01N 2201/127; A01B 76/00; A01B 79/005; A01C 7/10; A01C 21/007; G01J 3/0205; G01J 3/0289; G01J 3/18; G01J 3/44; G01J 3/502; G01J 2003/1861
See application file for complete search history.

(56) References Cited

U.S. PATENT DOCUMENTS 5,038,040 A     8/1991  Funk et al.
5,139,335 A *   8/1992  Lundeen ............... G01J 3/1838
                                                        356/328
(Continued)

FOREIGN PATENT DOCUMENTS

DE     102013208680 A1    11/2014
EP        1053671 A1      11/2000
(Continued)

OTHER PUBLICATIONS

European Search Report issued in counterpart application No. 18185776.4 dated Dec. 3, 2018. (8 pages).
(Continued)

*Primary Examiner* — Tarifur R Chowdhury
*Assistant Examiner* — Jonathon Cook
(74) *Attorney, Agent, or Firm* — Hanley, Flight & Zimmerman, LLC (57) ABSTRACT

In one embodiment, an agricultural sampling apparatus is provided. The apparatus comprising: a wave emitter; a wave transmitter configured to direct the waves from the wave emitter as a plurality of linewise waves to irradiate surface points of the agricultural sample; a dispersive element configured to receive waves arriving from the sample and deflect the arriving waves in at least two directions depending upon the wavelength of an arriving wave; and a detector configured with a plurality of detection elements disposed in at least two dimensions, the detector configured to convert the waves arriving from the dispersive element to a signal.

17 Claims, 4 Drawing Sheets

(51) Int. Cl.
  *G01N 21/25* (2006.01)
  *G01N 33/00* (2006.01)
  *A01B 76/00* (2006.01)
  *A01C 7/10* (2006.01)
  *G01N 21/65* (2006.01)
  *G01J 3/02* (2006.01)
  *G01J 3/18* (2006.01)
  *G01J 3/44* (2006.01)
  *A01C 21/00* (2006.01)
  *G01N 33/24* (2006.01)
  *A01B 79/00* (2006.01)

(52) U.S. Cl.
  CPC .......... *A01C 21/007* (2013.01); *G01J 3/0205* (2013.01); *G01J 3/0289* (2013.01); *G01J 3/18* (2013.01); *G01J 3/44* (2013.01); *G01N 21/255* (2013.01); *G01N 21/65* (2013.01); *G01N 33/0098* (2013.01); *A01B 79/005* (2013.01); *G01J 2003/1861* (2013.01); *G01N 2033/245* (2013.01); *G01N 2201/063* (2013.01); *G01N 2201/127* (2013.01)

(56) References Cited

U.S. PATENT DOCUMENTS

| | | | | |
|---|---|---|---|---|
| 5,444,528 | A * | 8/1995 | Puschell | G01J 3/1256 356/301 |
| 5,914,779 | A * | 6/1999 | Kalshoven | G01N 21/6486 250/458.1 |
| 2004/0114139 | A1 * | 6/2004 | Florek | G01J 3/2803 356/328 |
| 2006/0164639 | A1 * | 7/2006 | Horn | G01J 3/2803 356/326 |
| 2007/0013908 | A1 | 1/2007 | Lee et al. | |
| 2012/0298847 | A1 * | 11/2012 | Hayashi | A01C 21/002 250/227.11 |
| 2014/0197335 | A1 * | 7/2014 | Jayasooriya | G01N 33/02 250/459.1 |
| 2015/0015697 | A1 * | 1/2015 | Redden | G01N 33/0098 348/89 |
| 2016/0349167 | A1 * | 12/2016 | Eising | G01J 3/44 |
| 2017/0089829 | A1 * | 3/2017 | Bartholomew | G01J 3/42 |
| 2017/0219433 | A1 * | 8/2017 | Okuno | G01N 21/359 |

FOREIGN PATENT DOCUMENTS

| | | |
|---|---|---|
| NL | 1015440 C | 12/2001 |
| WO | 2014023810 A1 | 2/2014 |

OTHER PUBLICATIONS

Kruse, Jens., et al. "Innovative methods in soil phosphorus research: A review." Journal of Plant Nutrition and Soil Science, Jan. 12, 2015, vol. 178, No. 1, pp. 43-88.

Luna, Aderval S., et al. "Classification of soil samples based on Raman spectroscopy and X-ray fluorescence spectrometry combined with chemometric methods and variable selection." Analytical Methods, 2014, vol. 6, No. 22, pp. 8930-8939.

* cited by examiner

AGRICULTURAL SAMPLING APPARATUS AND SYSTEM

RELATED APPLICATIONS

This document claims priority based on German Patent Application No. 102017213419.4, filed on Aug. 2, 2017, which is hereby incorporated by reference into this application.

TECHNICAL FIELD

The present disclosure concerns a agricultural sampling system for investigation of an agricultural sample.

BACKGROUND

One aim of precision agriculture is to achieve, with given means, a best possible result in growing plants. For this reason one seeks to optimize operating parameters such as seed depth, spacing, seed variety, type of fertilizer, application amount, etc., during sowing, fertilizing, spraying, etc., on the basis of previously obtained data, which are acquired by sensors or other procedures before or during the operation and which concern, for example, the soil type, soil humidity, and soil components, and/or the components of the substances to be applied (fertilizers, manure) and/or properties of the plants (state of growth, components).

Besides chemical analyses to determine the components of the soil, for example, phosphorus, potassium, or organic components, sensor-based procedures have been described; these are based, for example, on gamma spectrometers and optical spectrometers and detect soil components during the traverse over a field by means of sensor-detected signals and data derived therefrom so as to image them and/or to control a device for application of fertilizer on that basis (for example, German Patent Application No. DE 10 2013 208 680 A1). Similarly, sensors equipped with near-infrared spectrometers have been described for analysis of crop components (European Patent Application No. EP 1 053 671 A1) and manure (Netherlands Patent Application No. NL 1015440 C). However, some mineral components (for example, phosphorus and potassium) of soils and other substances like liquids (manure) are not easily detected by NIR spectroscopy.

Moreover, it was proposed to investigate the components of soils, phosphorus, with a Raman spectrometer (See generally US 2007/0013908 A1; J. Kruse et al., Innovative methods in soil phosphorus research: A review, J. Plant Nutr. Soil Sci. 2015, 178, 43-88 and S. Luna et al., Classification of soil samples based on Raman spectroscopy and X-ray fluorescence spectrometry combined with chemometric methods and variable selection, Anal. Methods, 2014, 6, 8930-8939). In Raman spectroscopy the sample is irradiated with light, and inelastic light scattering, which is caused by an energy conversion of the stimulation wavelength to rotational and vibrational oscillations of surface molecules in the sample or vice versa, is detected and analyzed. The wavelength shift is specific for the type of molecule and can be used to identify it.

SUMMARY

Various aspects of examples of the present disclosure are set forth in the claims. In one embodiment, an agricultural sampling apparatus is provided. The apparatus comprising: a wave emitter; a wave transmitter configured to direct the waves from the wave emitter as a plurality of linewise waves to irradiate surface points of the agricultural sample; a dispersive element configured to receive waves arriving from the sample and deflect the arriving waves in at least two directions depending upon the wavelength of an arriving wave; and a detector configured with a plurality of detection elements disposed in at least two dimensions, the detector configured to convert the waves arriving from the dispersive element to a signal.

In another embodiment, an agricultural sampling system for performing tasks in a field is provided. The sampling system comprising: at least one drive module having a frame, ground engaging element and a power source; a spectrometry device positioned in a spaced relationship to the frame to analyze agricultural samples as the sampling system moves through the field. The spectrometer device comprising: a wave emitter; a wave transmitter configured to direct the waves from the wave emitter in linewise waves to irradiate a surface of the sample; a dispersive element configured to receive waves arriving from the sample and deflect the arriving waves in at least two directions depending upon the wavelength of an arriving wave; and a detector configured with a plurality of detection elements disposed in at least two dimensions, the detector configured to convert the waves arriving from the dispersive element to a signal. The sampling system further comprising a computing element in communication with the spectrometry device, the computing element using the output signals of the spectrometer system to generate a georeferenced recording of output signals of the spectrometer system.

BRIEF DESCRIPTION OF THE DRAWINGS

The above-mentioned aspects of the present disclosure and the manner of obtaining them will become more apparent and the disclosure itself will be better understood by reference to the following description of the embodiments of the disclosure, taken in conjunction with the accompanying drawing, wherein.

DETAILED DESCRIPTION

In investigations of agricultural samples, such as soil, generally a single point on the sample is irradiated with light. As a rule, the sample is composed of relatively small particles, the measurements of which lie in the mm range or smaller. If one selects the diameter of the stimulation light spot to be smaller than the particle size, one does not necessarily obtain results that might be representative and correct for the entire sample, because the measured surface area is smaller than the particle size. Accordingly, a very large number of measurement values would be acquired to achieve meaningful results, which makes the measurement time unreasonably long. Alternatively, the stimulation light spot could be selected to be larger than the particle size, but this brings the disadvantage that nonrepresentative particles (in the case of analysis of a grain sample, for example, nongrain components) may be analyzed, too, which distorts the measurement result. This problem exists in any kind of dispersive spectroscopy used for investigation of biological or geological samples, i.e., not just with Raman spectroscopy, but also with optical spectroscopy in the (near) infrared or visible wavelength range, in which the sample is irradiated with broadband light and the light reflected or transmitted by the sample is analyzed in wavelength resolution.

A agricultural sampling system, utilizing for example a spectrometer, would comprise a source of waves (for example electromagnetic waves from one or more LEDs or laser diodes), a wave transmitter for transmission of the waves from the source to the sample (for example, a lens or a glass fiber cable), a dispersive element (for example, a grating or a prism), which receives reflected or transmitted waves arriving from the sample and deflects the arriving waves in different spatial directions in dependence on wavelength, and a detector with a plurality of detection elements for conversion of the waves arriving from the dispersive element to electric signals. The transmitter is designed to irradiate the sample with the electromagnetic waves in lines and the detection elements of the detector are two dimensionally disposed.

In this way the electromagnetic waves coming from different points of the sample that is linewise irradiated with electromagnetic waves arrive along a first direction at different detection elements of the detector and, because of the wavelength-dependent deflection caused by the dispersive element, arrive along a second direction at different detection elements of the detector. The sample is thus spectrally analyzed along the linewise irradiation, which avoids or at least reduces the problems mentioned above.

In other words, the electromagnetic waves generated by the source, which can be visible light or waves in a higher or lower frequency range (UV, (N)IR, or microwaves), are not projected (imaged) onto the sample by the transmitter in a circular or point form (so-called zero-dimensional), as in the prior art, but rather in a line form (one-dimensional). For example, a cylindrical lens, prism, and/or a deflecting or directing element for the electromagnetic waves, which moves back and forth or rotates, for example, a mirror, can be used for this. The measurement of the irradiated region of the sample perpendicular to the lengthwise direction of the line can be chosen to be as small as possible, so that as far as possible only one particle of the biological or geological sample is irradiated in the transverse direction at one time. The waves reflected or transmitted by the sample are deflected by the dispersive element in different spatial directions. The detection elements of the detector are two dimensionally disposed, where a first direction corresponds to the lengthwise direction of the irradiated region of the sample and the second direction corresponds to the dispersion of the dispersive element. The spectrometer according to the present disclosure thus corresponds to a side by side arrangement of any desired large number of simple spectrometers along the irradiated region of the sample, so that many spectra can be obtained from the tested region of the sample at the same time. The individual spectra each represent relatively small regions of the sample, which can be smaller than the particle size of the sample, thus improving the measurement precision of the spectrometer and ensuring results that are representative of the entire sample. Moreover, there is the possibility of excluding nonrepresentative spectra (outliers) from the evaluation.

The source can irradiate the sample with broadband light, the spectrum of which can lie in the far and/or near infrared and/or visible wavelength range (see European Patent Application No. EP 1 053 671 A1) to evaluate certain components of the sample using the spectra by means of an evaluation device and an existing calibration. In another embodiment the source is monochromatic and a filter that is (almost) impermeable for the wavelength of the source can be inserted between the sample and the detector. This embodiment is a Raman spectrometer, in which it is also possible to determine the number of certain components in the sample by means of an evaluation device and an existing calibration. It is also possible that the wavelength of the source can be switched among a plurality of wavelengths, to switch between a detection of Stokes scattering and anti-Stokes scattering. The filter, which can be a narrow-band or an edge filter, can also be exchangeable. The detector can acquire a plurality of orders of the dispersed waves.

In addition, the detector can be connected to an evaluation unit, the housing of which is spatially separate from a housing containing the source, the transmitter, the dispersive element, and the detector, and which is connected to the latter housing by a mechanical and/or electrical connection that parts if overstressed.

The spectrometer system can be used in a stationary or in conjunction with a drive module such as a tractor in mobile mode, to investigate a stationary sample, or the sample is passed by the spectrometer system (or vice versa), for example on an agricultural field, to evaluate soil properties and components of the soil by means of the detected spectra. It can also be used to investigate the components (for example potassium or phosphorus) of other gaseous, solid, or liquid samples (for example manure, liquid fertilizer, spray agents, plants or crop), whether as a portable device or mounted on a machine for transport and/or application of the liquid or on a harvesting machine. The detected components and/or data of the sample derived therefrom can be imaged in georeferenced form by a computer device and/or used to control an agricultural machine, for example, to control the application of fertilizers, spray agents, seed, silage, etc.

Figure 1:
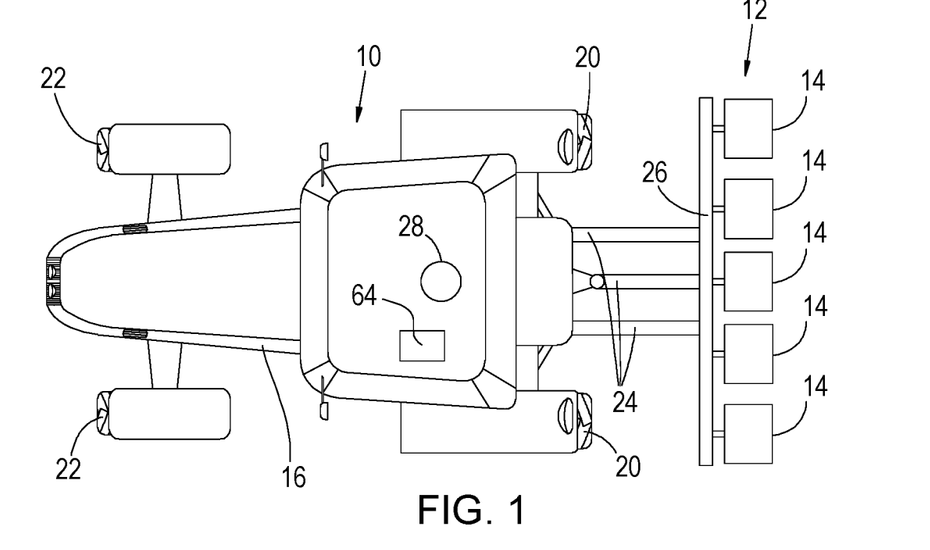
FIG. 1 shows a top view of a tractor with an attached seeder.

FIG. 1 shows a top view of a combination of a tractor 10 and a seeder 12, attached thereto, with a number of row units 14 distributed over the width of the unit 12 for introduction of seed into the soil, although any other type of seeder 12 could also be used. The row units 14 can lie on a single line as shown or can be mounted offset from each other in the forward direction. The tractor 10 comprises a chassis 16 with rear, drive wheels 20 and front, steerable wheels 22. A tool carrier 26 which extends horizontally and across the forward direction of the tractor 10, which runs from right to left in FIG. 1, is mounted on a three-point hitch 24 with upper and lower arms, which is attached to chassis 16. The tool carrier 26 holds the row units 14 of the seeder 12. The seeder 12 could also be attached to chassis 16 in any other way, for example it could rest on a vehicle chassis and be pulled by a draw bar. The seeder 12 could also be designed as a pneumatic seeder. A position determining device 28, which is based on reception of satellite signals (GPS, Galileo and/or Glonass and, possibly a local correction signal), is mounted on the roof of the tractor 10.

Figure 2:
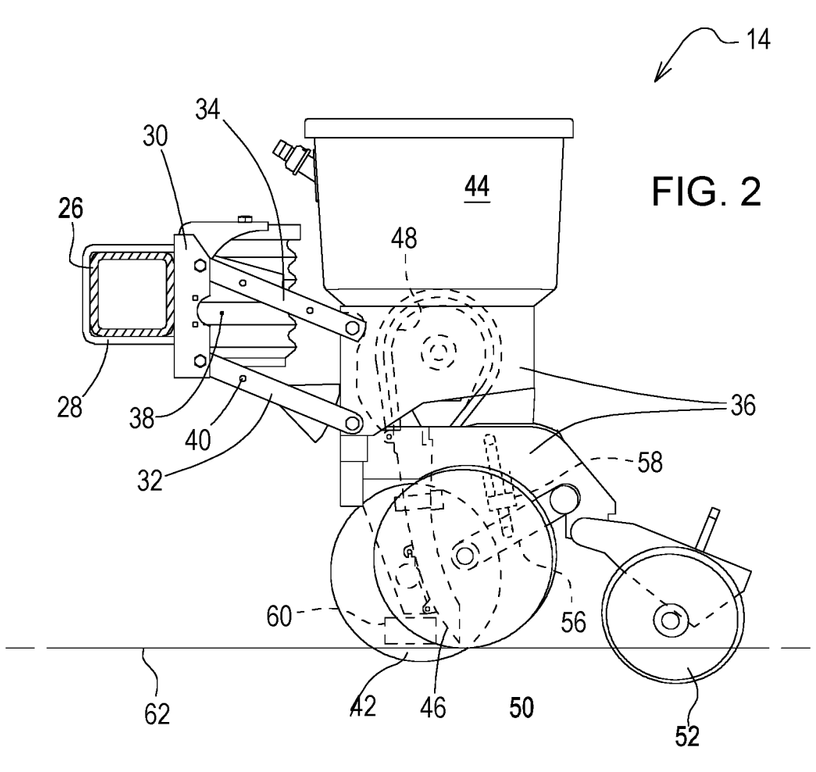
FIG. 2 shows a side view of a row unit of the seeder equipped with a spectrometer device.

FIG. 2 shows a row unit 14 of the seeder 12. The row unit 14 is mounted on the tool bar 26 via U-shaped brackets 28, which are connected to a console 30, which extends vertically at the rear of the tool bar 26 and is hinged to the two hinge arms 32, 34, which are mounted one above the other and which are also each hinged to a frame 36 of the row unit 14. The hinge arms 32, 34 with the console 30 and the frame 36 form an adjustable parallelogram, which determines the height of the frame 36 above the ground. A pneumatic actuator 38, which serves as tensioning agent and which is designed as a pneumatic bellows cylinder in the embodiment that is shown, engages the console 30 at the top on the one hand and the lower hinge arm 32 at the bottom on the other (at point 40) and determines the position of the frame 36 and the force with which a furrow opener 42 supported on frame 36 interacts with the soil.

In a substantially known way the frame 36 carries a seed tank 44, a seed tube 46, and a metering device 48 (a pneumatic device operating with reduced pressure provided by a blower, which is not shown), which delivers individual seeds from the seed tank 44 one at a time to the seed tube 46, which deposits the seed in a furrow, which is made by the furrow opener 42, the operating depth of which is set by a gauge wheel 50. The furrow is closed by a closing wheel 52. The vertical position of a swing arm 56 holding the gauge wheel 50, and thus the depth of the furrow in which the seed is deposited, is determined by an actuator 58. A feedback sensor, not shown, can detect the current seed depth.

An agricultural sampling system 60—which may be a spectrometer system 60—interacts with the soil 62 and with a furrow produced by furrow opener 42, is mounted at the lower end of frame 36 in front of the seed tube 46. The spectrometer system 60 optically determines properties of the soil 62, for example about its components, and transmits its measurement values to a computer device 64 of tractor 10. There, using the signals from the position determining device 28, they are stored in georeferenced fashion for planning subsequent work operations and/or serves to control an actuator, for example the actuator 58 for specifying the seed depth. The mounting of the spectrometer system 60 that is shown is only one embodiment example. The spectrometer system could be mounted on any other (agricultural) machine and be moved by it over the soil 62 to determine its properties. Also, it could be used in stationary or mobile mode to test soil samples, or it can be used for analysis of the components of any other materials (for example, manure, solid or liquid fertilizers, or plants to be sprayed or fertilized, or crop to be harvested or that has been harvested). The data obtained concerning the components can serve to control actuators, for example for application of auxiliary agents such as fertilizers or spray agents, or can be stored in georeferenced form, to be used for precision agricultural purposes.

Agricultural Sampling System

Figure 3:
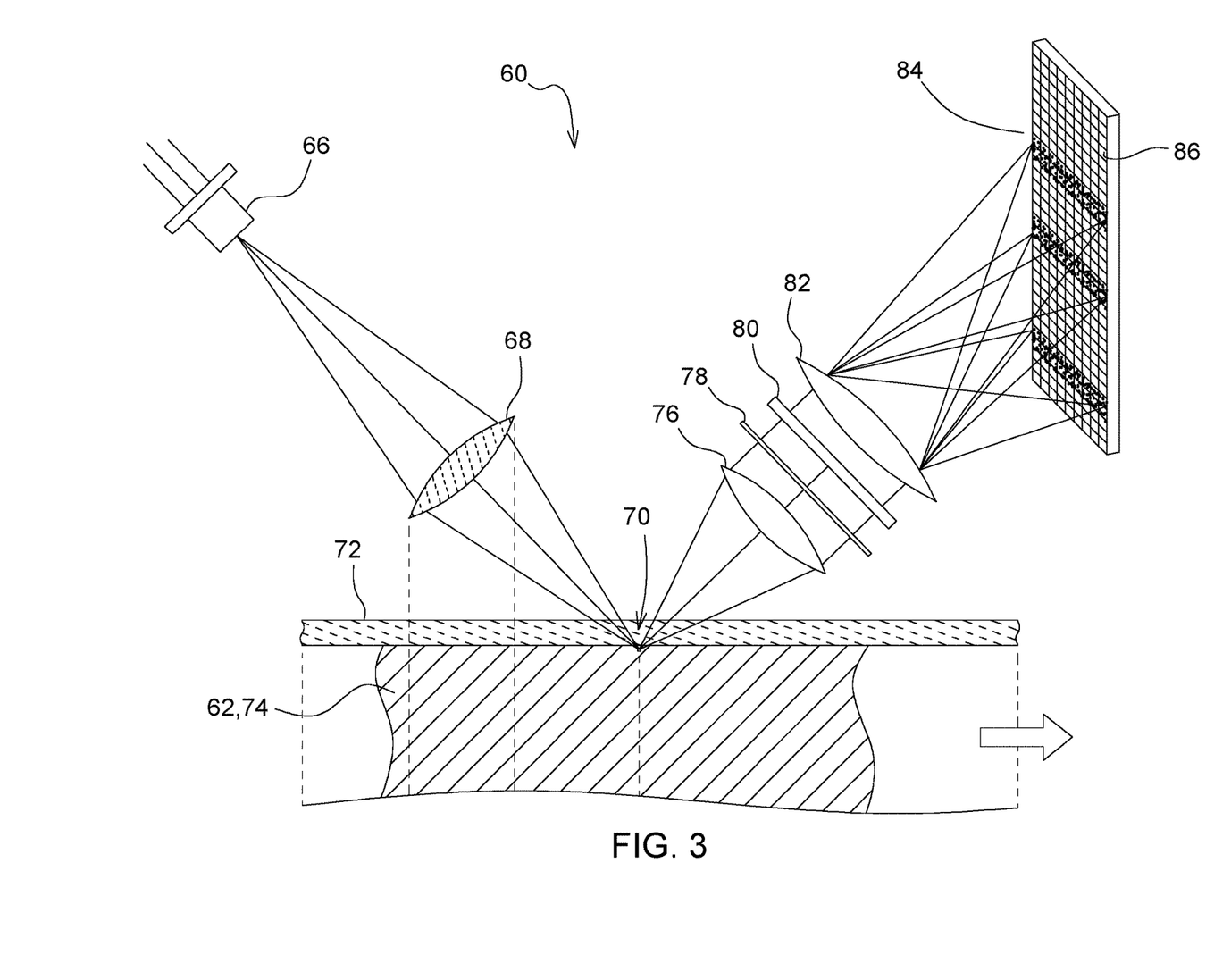
FIG. 3 shows a schematic side view of the spectrometer device.
Figure 4:
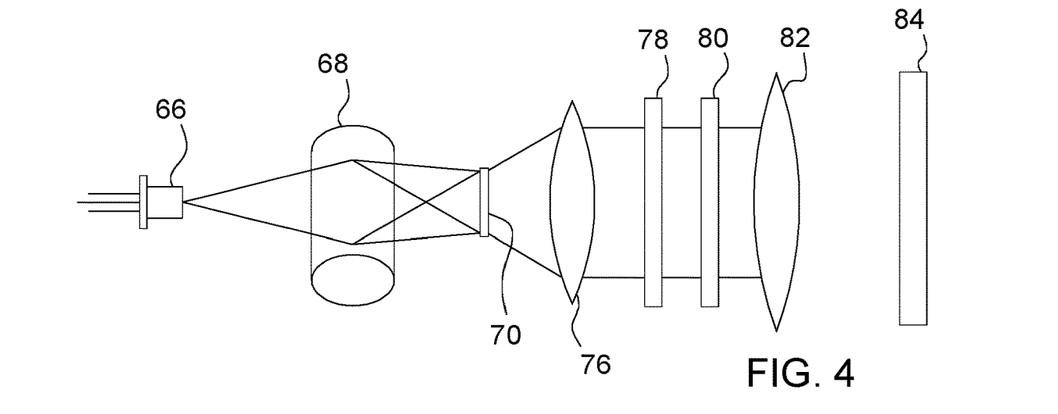
FIG. 4 shows a top view of the spectrometer device.

Reference is now made to FIGS. 3 and 4, in which the structure of spectrometer system 60 is shown in more detail. The spectrometer system 60, which is designed as a Raman spectrometer in this embodiment, comprises a wave emitter 66 as a source of electromagnetic waves, which can be a laser diode; a wave transmitter 68, for example in the form of a cylindrical lens, which serves to direct the electromagnetic waves from the wave emitter 66 through a window 72, which is permeable to the waves, to an irradiated surface 70, which is on the outside of the window 72 (and thus outside the spectrometer system 60), on a sample 74 that is to be tested, and to focus them on the surface 70. The electromagnetic waves from the wave emitter 66 can lie in the visible or (near) infrared region. The sample 74 can be the soil sample 62, as shown in the embodiment example in FIG. 2, or any other biological or geological sample 74. The transmitter 68 are designed so that the area 70 is irradiated in lines, as shown in FIG. 4. Additional methods (for example lenses, prisms, movable elements, or the like), not shown in FIGS. 3 and 4, could also be used to fan out the waves, which arrive from the nearly spot-shaped wave emitter 66 and run approximately parallel to each other, into lines.

The window 72 can be made of sapphire glass to keep abrasion by the sample 74 low. Unlike shown in FIG. 3, the irradiated surface 70 can be situated at a certain distance, a few mm or cm, from window 72.

Moreover, for analysis of electromagnetic waves reflected by the sample 74 and arriving back into the spectrometer system 60 through the window 72, the spectrometer system 60 contains a dispersive element 80 in the form of a grating (or prism) and a detector 84 with detection elements 86, which convert the electromagnetic waves reaching it to electric signals. The grating can be made as a mirror grating or holographic grating. The detector 84 can be made as a CCD or photodiode array. A lens 76, which shapes the diverging waves arriving from sample 74 into parallel waves, can be disposed between the sample 74 and the dispersive element 80, and a focusing optical system 82, one that images the dispersive element 80 onto the detector 84) can be mounted between the dispersive element 80 and the detector 84. A filter 78 can be disposed in front of or behind the dispersive element 80, to filter out or damp wavelengths of the monochromatic wave emitter 66 that interfere with the evaluation of the spectra. The lens 76 and the focusing optics 82 can be spherical or aspherical lenses or more complex multilens structures or other optical elements.

The lengthwise axis of the cylindrical lens serving as transmitter 68 extends across the plane of the drawing of FIG. 3 and vertically and thus parallel to the lengthwise direction of the irradiated surface 70 in the plane of the drawing of FIG. 4. The grating slots of the dispersive element 80 likewise extend across the plane of FIG. 3. The optical axes of the lens 76 and the focusing optics 82 lie in the plane of FIG. 3.

Mode of Operation

Considering the foregoing, the sample 74 is irradiated with monochromatic waves (light) within a line-shaped surface 70. The waves reflected by the sample 74 travel to the dispersive element 80 and are deflected by it in wavelength-dependent directions, i.e., dispersed at different angles in the plane of the drawing of FIG. 3. In this way the detection elements 86 of the detector 84 receive, along the plane of the drawing of FIG. 3 (which within the scope of this disclosure is called the second direction), different intensities, which are dependent on the relevant wavelength. Accordingly, a spectrum is detected in each of the detection elements 86 of FIG. 3, which lie one above the other. Because of the line-shaped irradiated surface 74, plural independent spectra, each of which represents different points on sample 74, arise on the detector 84 in the direction perpendicular to the plane of the drawing of FIG. 3 (which within the scope of this disclosure is called the first direction).

Accordingly, the spectrometer system 60 simultaneously detects the spectra of a plurality of relatively small regions of sample 74, which lie side by side. Through this a sufficient light intensity is enabled and at the same time it is ensured that in the evaluation of the signals of the detection elements by an evaluation unit, which is not shown in the FIG. 3 and which can be spatially integrated into the spectrometer system 60 in the same housing or can be separate therefrom (for example integrated into the computer unit 64 or on a separate computer, which can receive the intermediately stored signals of the detection elements 86 by remote data transfer or a portable memory card), non-representative regions of the sample 74, which can be detected by spectra acquired by the detection elements 86 along the second direction, which differ significantly (by more than a threshold value) from the spectra that are generated in the other regions of the sample 74 and are acquired by the other detection elements 86 of the detector 84 along the second direction, can optionally be discarded in the evaluation of the components, or their distorting effect on the result will be at least attenuated by averaging. An averaging of the individual spectra or the calculated components, which are determined by means of the individual spectra and a calibration, can take place.

Figure 5:
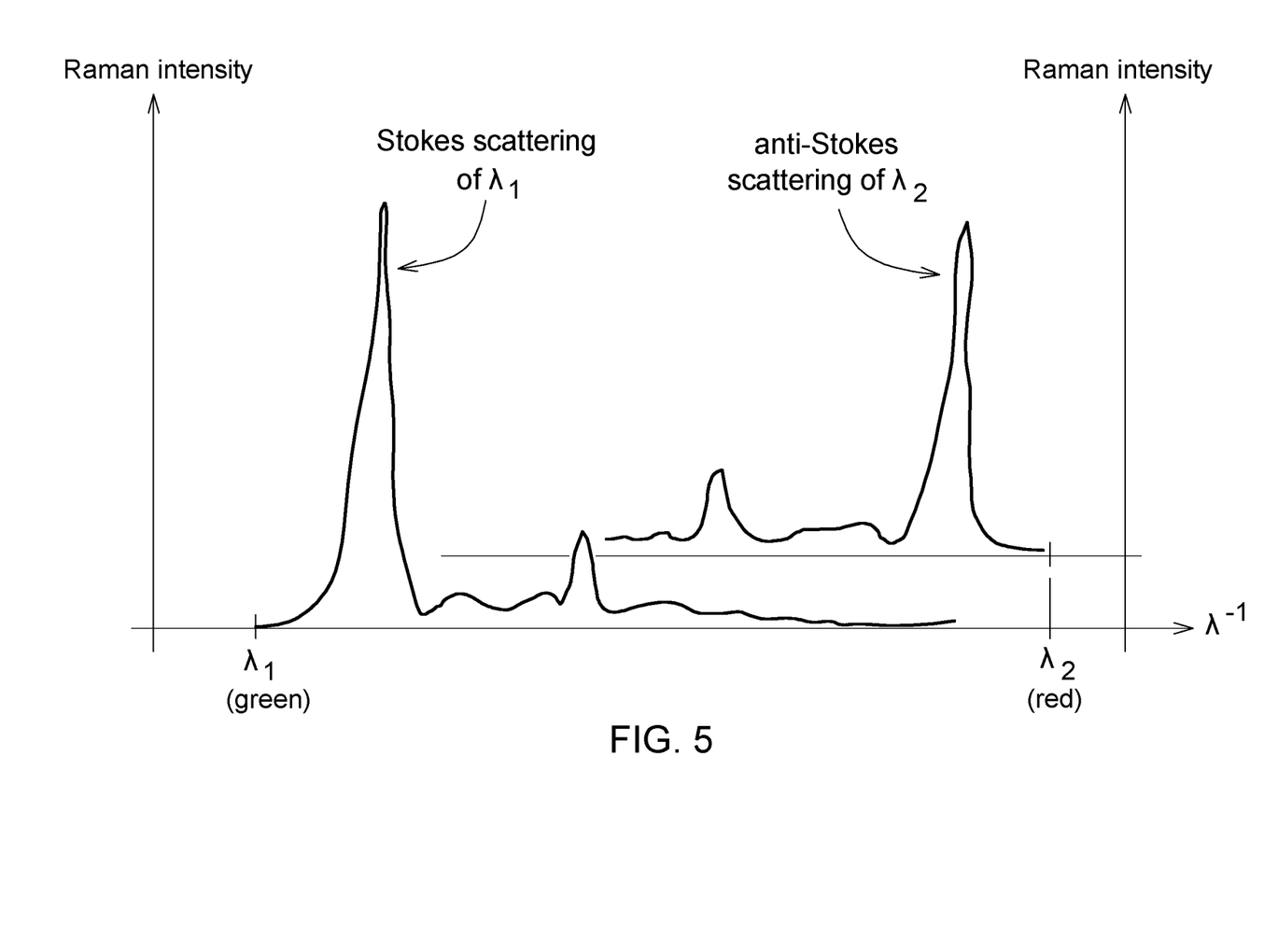
FIG. 5 shows an example of spectra acquired by the spectrometer device at different stimulation wavelengths.

FIG. 5 shows as an example a spectrum acquired by detector 84 through its detection elements 86 along the second direction (the X axis is proportional to wave number or $1/\lambda$), in which the sample 74 is irradiated by the wave emitter 66 with a monochromatic (here: green) wavelength $\lambda_1$. The stimulation wavelength $\lambda_1$ of wave emitter 66 is filtered out or damped by the filter 78 and the spectrum comprises essentially the so-called Stokes scattering stimulated by the wavelength $\lambda_1$, which arises because vibrational and rotational modes of surface molecules of the sample 74 are stimulated, due to which the waves reflected by the sample 74 are longer than the wavelength $\lambda_1$ and, because of energy transfer to the stimulation modes of the molecules, contain less energy.

FIG. 5 additionally shows a second spectrum, in which the sample 74 is irradiated with a monochromatic (here: red) wavelength $\lambda_2$ by the wave emitter 66. The stimulation wavelength $\lambda_2$ of the wave emitter 66 is filtered out by the filter 78 (now a different filter) and the spectrum essentially comprises the so-called anti-Stokes scattering stimulated by wavelength $\lambda_2$, which arises because the waves reflected by the sample acquire additional energy of vibrational and rotational modes of surface molecules of sample 74, due to which the waves reflected by the sample 74 are shorter than the wavelength $\lambda_2$ and, as a consequence of energy transfer from the stimulation modes of the molecules, contain more energy.

It would also be possible to stimulate and analyze both the anti-Stokes scattering and the Stokes scattering with a single wavelength that lies between wavelength $\lambda_1$ and $\lambda_2$.

Other Embodiments

Accordingly, it is conceivable to make the wavelength emitted by the wave emitter 66 switchable, for example to be able to evaluate the Stokes scattering or the anti-Stokes scattering in each case according to application or to operate normally at a first short wavelength and to be able to switch to a longer wavelength that does not generate fluorescence, if fluorescence should arise. For this the wave emitter 66 could comprise two or more different generators of electromagnetic waves, between which a switch can be made electrically and/or by mechanical movement, so that the same surface 70 is always irradiated regardless of the wavelength. The filter 78 would then also need to be changed, for which an appropriate actuator can be provided, or a single filter 78 that filters out or damps both wavelengths of the sources 66 can be used, or two filters 78 can be disposed one behind the other, of which in each case one filters out or damps one of the wavelengths of sources 66. Narrow band or edge filters could also be used. The filter 78, which reduces the intensity of the stimulation wavelength by several powers of ten, to enable a referencing of the wavelength of the wave emitter 66 and its intensity for the evaluation of the spectra, damps in the region of the relevant stimulation wavelengths. The wavelengths to be tested are, however, transmitted by the filter or filters 78.

Shorter stimulation wavelengths have advantages in Raman spectroscopy, but are not always used, for example, due to the occurrence of fluorescence. Longer stimulation wavelengths have energy disadvantages, but in certain applications are the only solution to be able to perform Raman spectroscopy. The stimulation wavelengths of the sources 66 can be set at the beginning and at the end of the spectral region that can be processed by the spectrometer system 60. When the wave emitter 66 is operated at the shorter wavelength, Stokes scattering is utilized, and when the wave emitter 66 operates at the longer wavelength, anti-Stokes scattering is used. The sources 66 are accordingly activated alternatingly and not at the same time.

The spectral region that is optimally used by the spectrometer lies, for example, between about 650 nm and about 900 nm. A wave emitter 66 in the form of a semiconductor laser with 660-nm wavelength could serve for stimulation of the Raman spectrum that utilizes Stokes scattering and lies in the range of 665 nm to 850 nm for the substances of interest. The second wave emitter 66, in the form of a second stimulation laser, could lie at about 900 nm. The Raman spectrum from the anti-Stokes scattering would then utilize the 895 nm to 700 nm range. Similar but not identical information about the sample is found in the Stokes scattering and in the anti-Stokes scattering. Specific information can be obtained by the change of the stimulation wavelengths. The sources 66 could be driven alternatingly or a change of the stimulation wavelengths takes place (automatically, depending on the detected spectrum), for example to prevent fluorescence that may arise. The filter for damping the laser wavelength in this embodiment can be an edge filter and need not be a very narrow band filter (as when a plurality of orders is used, as described in the following paragraph). Besides the avoidance of fluorescence that was already noted, skillful choice of the stimulation wavelength can result in the Raman spectrum lying in the most sensitive spectral region of the detection system.

Figure 6:
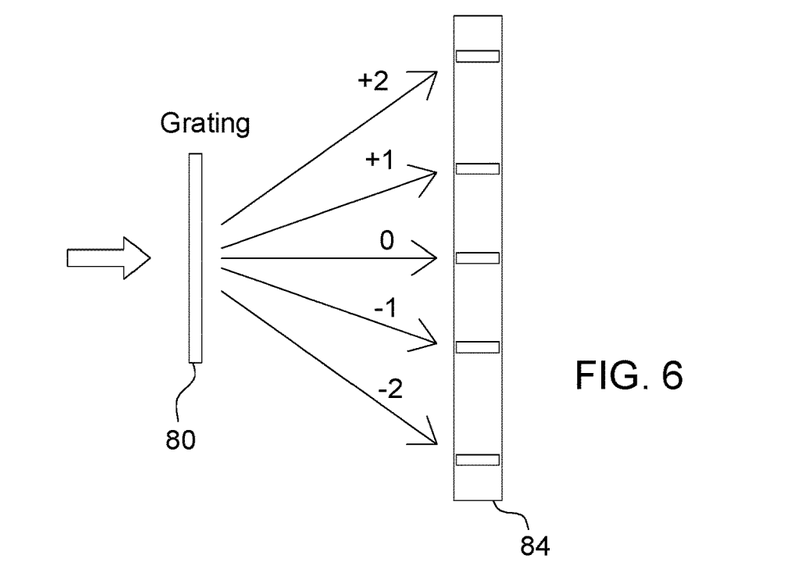
FIG. 6 shows a schematic drawing of diffraction orders.

Furthermore, it would be conceivable for the dispersive element 80 and the detector 84 to be designed as shown in FIG. 6, i.e., the detector 84 detects not only the zeroth and first diffraction order, but rather also the second diffraction order and possibly still higher diffraction orders. A wavelength of wave emitter 66 can be optimally utilized with each order. Moreover, all the information about the sample 74 that is provided by detector 84 is evaluated by the evaluation of the higher orders.

Figure 7:
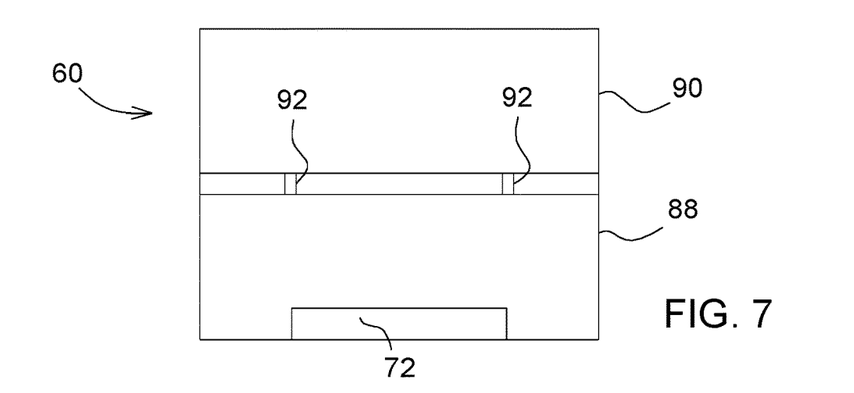
FIG. 7 shows a schematic side view of the housing of the spectrometer with another housing in which an evaluation unit is accommodated.

Finally, in FIG. 7 it is shown that the spectrometer system 60 can be accommodated in a housing with a first part 90 and a second part 88. The second, lower part 88 contains the optical elements (shown in FIGS. 3 and 4) of the spectrometer system 60, including the wave emitter 66 and the detector 84 and an associated analog-digital converter for digitization of the signals of the detection elements 86 and a memory with identification data and/or specific parameters of the spectrometer system 60, which are used, for example, by the evaluation unit described above for evaluation of the signals of the detection elements 86, while the first, upper part 90 comprises the evaluation unit needed to evaluate the signals of the detector 84, a memory, power supply, and an interface for the computer device 64. The first part 90 is mounted permanently on the agricultural machine (for example as in FIG. 2 on frame 36 of the row unit 14 of the seeder 12) and is connected to the second part 88 by a connection that separates if overstressed, in the form of a preset breaking site, which can be realized, for example, by shear pins 92. If then the second part 88 is damaged in the case of unexpected soil contact, the breaking site separates and the first part 90 remains intact. In this case an electrical plug connection between the first part 90 and the second part 88, which is not shown in FIG. 7, also separates.

One could also separate the two parts 90 and 88 spatially farther apart. Thus, the first part 90 could be accommodated on board the tractor 10 or higher up on the seeder 12 and be linked by an electrical cable to the second part 88, which would be supported in such an embodiment directly or indirectly on frame 36 of the seeder 12 and would be connected to the frame 36 by a connection that separates upon overstress in the form of a preset breaking site. In this case a plug connection of the connecting cable between the two parts 90 and 88 would also separate. In this way it will be guaranteed in this embodiment, too, that at most the second part 88 would need to be replaced.

It should be further noted that the two-part housing of FIG. 7 can also be used with the spectrometer systems 60 whose detector 84 comprises only a single row of detection elements 86. The same applies to the said switchable wavelength and the use of a plurality of orders.

The incident and exit angles of the waves at the sample 74 need not, as shown in FIG. 3, each be about 45°, rather they can deviate therefrom and even be asymmetric.

The width of the surface 70 in the horizontal plane of the drawing of FIG. 3 can be constant or can be variable by adjusting the transmitter 68, for example for adjustment to the particle size of the sample 74. However, it would also be conceivable to set a fixed gap between the wave emitter 66 and the sample 74 which compensates or supplements the transmitter 68. If the gap has a waist or is designed as a triangle or is stepped, the width of the surface 70 in the horizontal plane of the drawing of FIG. 3 can vary over the length of the surface 70 to be able to vary or optimize the resolution and sensitivity of the spectrometer system 60. The change of the width of the inlet slit can take place successively in time or each spectrum or group of spectra can have simultaneously different widths.

The terminology and headings used herein is for describing particular embodiments only and is not intended to be limiting of the invention. While the description of the present invention has been presented for purposes of illustration and description; it is not intended to be exhaustive or limited to the invention in the form disclosed. Many modifications, variations, alterations, substitutions or equivalent arrangements not hereto described will be apparent to those of ordinary skill in the art without departing from the scope and spirit of the invention. Additionally, while the various embodiments of the invention have been described, it is to be understood that aspects of the invention may include only some of the described embodiments. Accordingly, the invention is not to be limited by the foregoing description, but is only limited by the scope of the appended claims.

The invention claimed is:

1. A spectrometer system comprising:
a wave emitter;
a wave transmitter configured to direct waves from the wave emitter to irradiate surface points of an agricultural sample;
a dispersive element configured to receive the waves arriving from the agricultural sample and deflect the waves in at least two directions depending upon a wavelength of the waves;
a detector configured with a plurality of detection elements disposed in at least two dimensions, the detector configured to convert the waves arriving from the dispersive element to a signal, the waves to leave one or more of the surface points of the agricultural sample in first and second directions relative to the plurality of detection elements, the detection elements disposed in a first dimension corresponding to a lengthwise direction of the one or more surface points of the agricultural sample and in a second dimension corresponding to a dispersion of the dispersive element and
an evaluation unit connected to the detector, the evaluation unit configured to calculate a calibration using the signal and first spectra acquired by at least one of the plurality of detection elements along the second dimension that differ from second spectra that are acquired along the second dimension by at least one different detection element of the detector.

2. The spectrometer system of claim 1, wherein the wave emitter includes a spot source and the wave transmitter is configured to image the spot source on the surface points of the agricultural sample.

3. The spectrometer system of claim 2, wherein the wave emitter is monochromatic.

4. The spectrometer system of claim 3, wherein the wavelength is adjustable between a plurality of wavelengths.

5. The spectrometer system of claim 1, wherein the dispersive element is a grating.

6. The spectrometer system of claim 1, further including an adjustable filter positioned between the agricultural sample and the detector, the adjustable filter being at least approximately impermeable for the wavelength.

7. The spectrometer system of claim 6, wherein the adjustable filter is at least one of a narrow-band filter or an edge filter.

8. The spectrometer system of claim 1, wherein the evaluation unit is disposed in a first housing spatially separate from a second housing in which the wave emitter, the wave transmitter, the dispersive element, and the detector are disposed, the first and second housings being connected by at least one of a mechanical or electrical connection and configured to separate upon a stress threshold.

9. An agricultural sampling system for performing tasks in a field, the agricultural sampling system comprising:
at least one drive module having a frame, a ground engaging element and a power source;
a spectrometer system positioned in a spaced relationship to the frame to analyze an agricultural sample in the field, the spectrometer system including:
a wave emitter,
a wave transmitter configured to direct waves from the wave emitter to irradiate a surface of the agricultural sample,
a dispersive element configured to receive the waves arriving from the agricultural sample and deflect the waves in at least two directions depending upon a wavelength of the waves,
a detector configured with a plurality of detection elements disposed in at least two dimensions, the detector configured to convert the waves arriving from the dispersive element to a signal, the waves to leave one or more surface points of the surface of the agricultural sample in first and second directions relative to the plurality of detection elements, the detection elements disposed in a first dimension corresponding to a lengthwise direction of the surface and in a second dimension corresponding to a dispersion of the dispersive element, and an evaluation unit connected to the detector, the evaluation unit configured to calculate a calibration using the signal and first spectra acquired by at least one of the plurality of detection elements along the second dimension that differ from second spectra that are acquired along the second dimension by at least one different detection element of the detector, and a computer device in communication with the spectrometer system, the computer device using output signals of the spectrometer system to generate a georeferenced recording of the output signals of the spectrometer system.

10. The agricultural sampling system of claim 9, wherein the spectrometer system is positioned on a tool bar connected to the frame of the at least one drive module.

11. The agricultural sampling system of claim 10, wherein the tool bar is a planter and the spectrometer system is positioned proximate a row unit of the planter.

12. The agricultural sampling system of claim 10, wherein the computer device uses the output signals of the spectrometer system to control an actuator associated with at least one of the at least one drive module or the tool bar.

13. The agricultural sampling system of claim 9, wherein the at least one drive module is a tractor.

14. A spectrometer system comprising:
a wave emitter;
a wave transmitter configured to direct waves from the wave emitter to irradiate surface points of an agricultural sample;
a dispersive element configured to receive the waves arriving from the agricultural sample and deflect the waves in at least two directions depending upon a wavelength of the waves;
a detector configured with a plurality of detection elements disposed in at least two dimensions, the detector configured to convert the waves arriving from the dispersive element to a signal, the waves to leave the surface points of the agricultural sample in a first direction and in a second direction relative to the plurality of detection elements, the plurality of detection elements disposed in a first dimension corresponding to a lengthwise direction of the surface points of the agricultural sample and in a second dimension corresponding to a dispersion of the dispersive element; and an evaluation unit connected to the detector, the evaluation unit configured to calculate a calibration using the signal of the detector and first spectra acquired by at least one of the plurality of detection elements along the second dimension that differ from second spectra that are acquired along the second dimension by at least one different detection element of the detector, the evaluation unit disposed in a first housing spatially separate from a second housing in which the wave emitter, wave transmitter, dispersive element, and the detector are disposed, the first and second housings being connected by at least one of a mechanical or electrical connection and configured to separate upon a stress threshold.

15. The spectrometer system of claim 1, further including a window proximate the agricultural sample, the waves to pass through the window to the agricultural sample, the window at least partially composed of sapphire glass.

16. The spectrometer system of claim 5, wherein the grating is at least one of a mirror grating or a holographic grating.

17. The spectrometer system of claim 4, further including a first filter and a second filter positioned between the agricultural sample and the detector, the first filter to damp a first wavelength from the plurality of wavelengths and the second filter to damp a second wavelength from the plurality of wavelengths, the first wavelength different from the second wavelength.

* * * * *